United States Patent [19]
Baylor et al.

[11] Patent Number: 5,457,313
[45] Date of Patent: Oct. 10, 1995

[54] FIBER OPTIC DETECTOR AND METHOD FOR USING SAME FOR DETECTING CHEMICAL SPECIES

[75] Inventors: Lewis C. Baylor, North Augusta, S.C.; Bruce R. Buchanan, Perkiomenville, Pa.

[73] Assignee: The United States of America as represented by the United States Department of Energy., Washington, D.C.

[21] Appl. No.: 189,823

[22] Filed: Feb. 1, 1994

[51] Int. Cl.⁶ .......................................... H01J 5/16
[52] U.S. Cl. .................. 250/227.21; 250/483.1; 422/82.05
[58] Field of Search ............... 250/226, 227.21, 250/227.23, 483.1, 459; 422/82.05, 86

[56]  References Cited

U.S. PATENT DOCUMENTS

| | | | |
|---|---|---|---|
| 3,114,610 | 12/1963 | Gafford et al. | 422/86 |
| 4,158,769 | 6/1979 | Smith | 250/255 |
| 4,198,568 | 4/1980 | Robbins et al. | 250/459 |
| 4,467,208 | 8/1984 | Muller et al. | 250/483.1 |
| 4,892,383 | 1/1990 | Klainer et al. | 250/227.21 |

OTHER PUBLICATIONS

Mimms, L. T., Spectrophotometric Study of Coverage and Acid–Base Equilibrium of a Chemically Bonded Base, Analytical Chem. vol. 89 1977 pp. 355–361.
G. B. Harper, Reusable Glass–Bound pH Indicators, Analytical Chemistry vol. 47 Feb. 1975 pp. 348–351.

*Primary Examiner*—Stephone B. Allen
*Attorney, Agent, or Firm*—Brian R. Tumm; Harold M. Dixon; William R. Moser

[57] ABSTRACT

An optical sensing device for uranyl and other substances, a method for making an optical sensing device and a method for chemically binding uranyl and other indicators to glass, quartz, cellulose and similar substrates. The indicator, such as arsenazo III, is immobilized on the substrate using a chemical binding process. The immobilized arsenazo III causes uranyl from a fluid sample to bind irreversibly to the substrate at its active sites, thus causing absorption of a portion of light transmitted through the substrate. Determination of the amount of light absorbed, using conventional means, yields the concentration of uranyl present in the sample fluid. The binding of uranyl on the substrate can be reversed by subsequent exposure of the substrate to a solution of 2,6-pyridinedicarboxylic acid. The chemical binding process is suitable for similarly binding other indicators, such as bromocresol green.

19 Claims, 1 Drawing Sheet

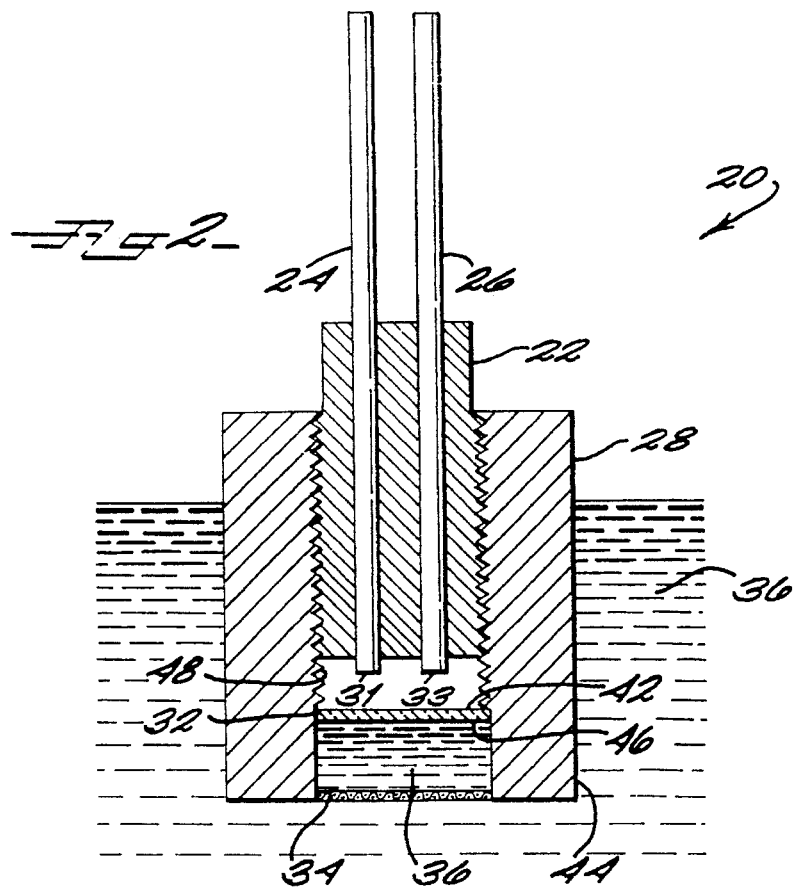
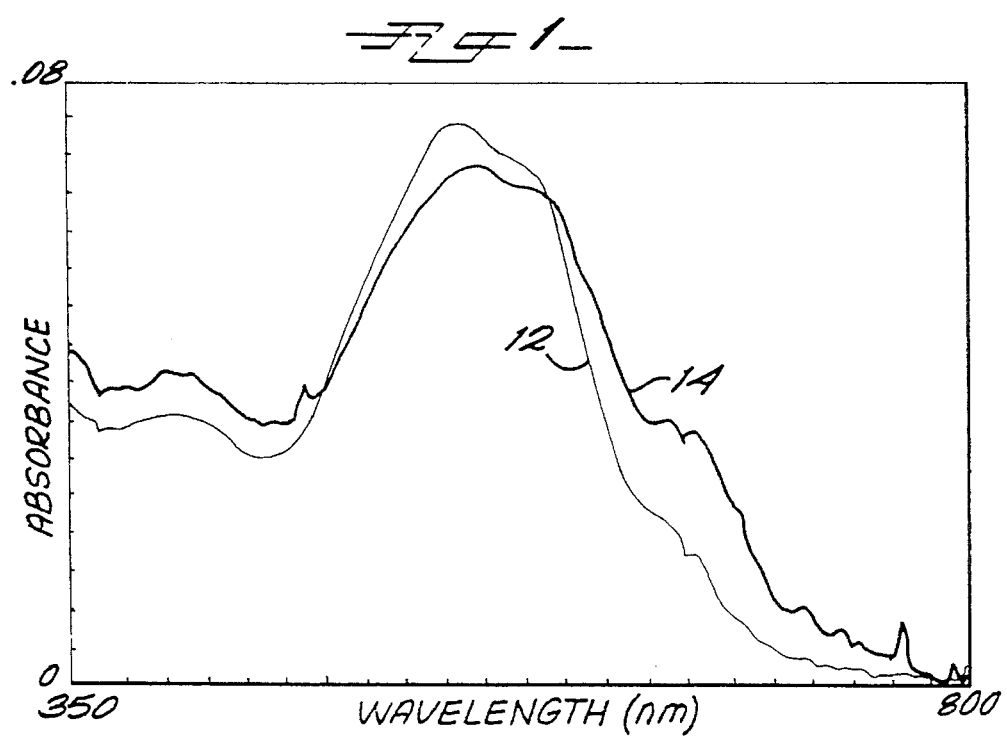

5,457,313

FIBER OPTIC DETECTOR AND METHOD FOR USING SAME FOR DETECTING CHEMICAL SPECIES

BACKGROUND OF THE INVENTION

1. Field of the Invention

The present invention relates to indicators for use in spectrophotometric detection of chemical compounds. More particularly, the present invention relates to binding arsenazo III and other indicators to substrates for use in spectrophotometric analysis. The United States Government has rights in this invention pursuant to Contract No. DE-AC09-898R18035 between the U.S. Department of Energy and Westinghouse Savannah River Company.

2. Discussion of Background

The use of indicators to facilitate visual identification of chemical compounds is well known. An indicator is typically a substance that undergoes a noticeable change, chemical or otherwise, in the presence of another material. For example, an indicator may luminesce, absorb light energy or change colors in the presence of a particular material of interest. Examples of materials measured include oxygen, carbon dioxide, hydrogen ions (pH), electrolytes, and glucose. Obviously, the properties of indicators make them useful in various types of sensing instrumentation.

In the past, indicators were used by dissolving them in a solution containing the material of interest or by applying them as a coating onto paper that was then put into contact with a fluid sample. However, such conventional testing methods destroy the fluid sample and indicator paper, and thus are non-reusable and often costly.

One of the more recent uses of indicators is with optical sensing devices. Optical sensing devices are well known for measuring the presence and concentration of a chemical compound in a medium, such as a solvent. When used with optical sensors, an indicator, often in combination with a sample-permeable matrix, is positioned to interact with the sample in the medium, which is near or adjacent to a transmitting optical fiber. The interaction between the indicator and the chemical to be sensed or measured alters the light being transmitted prior to its receipt by a receiving fiber. The indicator may absorb, reflect, refract, scatter, fluoresce, or emit Raman radiation in altering the incident light. By comparing the received light to the transmitted light, the concentration of the chemical compound being detected can be easily determined.

Various techniques for immobilizing indicators on substrates for use by instrumentation in detecting chemical compounds are known. In one specific instance, L. T. Mimms et al., in their article titled "Spectrophotometric Study Of Coverage And Acid-Base Equilibrium Of A Chemically Bonded Base", *Analytical Chemistry*, Vol. 89, pgs. 355–361 (1977), describe the immobilization of an aniline azo dye on a glass slide by reacting an organosilane reagent with the surface of the glass slide. Also, in an earlier, related article titled "Reusable Glass-Bound pH Indicators", *Analytical Chemistry,* Vol. 47, pgs. 348–351 (February 1975), G. B. Harper describes a chemical system in which a variety of pH indicators are immobilized on porous glass materials for use in optical absorption spectrophotometric analysis. Glass-bound pH indicators offer several advantages over conventional indicator applications, including the capability of repeated use, resistance to microbial attack, and insolubility such that samples and systems are not contaminated.

Several sensors are known for use in detecting radiation from, for example, uranium. For instance, see U.S. Pat. No. 4,467,208, issued to Mëiller et al., U.S. Pat. No. 4,198,568, issued to Robbins et al. and U.S. Pat. No. 4,158,769, issued to Smith.

Both Smith and Robbins et al. disclose methods for detecting uranium in solution. Robbins et al., illuminate a uranium-containing sample with ultraviolet light to cause uranium compounds to luminesce. Smith uses a series of filters to pass specific radiation through to a radiation counter.

There exists a need for indicators suitable for binding other compounds, including uranyl indicators, to substrates for spectrophotometric analysis.

SUMMARY OF THE INVENTION

According to its major aspects and broadly stated, the present invention is an apparatus and method for sensing uranyl and other substances using a substrate in which the indicator is chemically bound thereto. In particular, the present invention comprises an optical device for sensing uranyl, a method for making an optical device for sensing uranyl and a method for immobilizing indicators for uranyl and other components to glass, quartz, cellulose and related substrates using a chemical binding process. In a preferred use, the indicator reacts with the uranyl from a fluid sample to form a reaction product irreversibly on the substrate, thus causing absorption of a portion of light transmitted through the substrate. Determination of the amount of light absorbed, using spectrophotometric means, yields the concentration of uranyl present in the sample fluid. The indicator continues to form a reaction product with uranyl on the substrate until the substrate is saturated. Exposure of the substrate to 2,6-pyridinedicarboxylic acid frees the uranyl from the indicator, thus allowing the substrate to be used in future applications.

A major feature of the present invention is the use of a substrate, such as an optical lens assembly, having an indicator, such as arsenazo III, permanently affixed thereto for forming a reaction product on the lens assembly with a component of interest, such as uranyl, from a fluid sample being tested. The uranyl forms a reaction product with the arsenazo III and binds to its active site on the substrate in relation to its concentration in the fluid sample. The advantage of this feature is that it provides the ability to determine the concentration of uranyl in a fluid sample using well known spectrophotometric analysis techniques.

Another feature of the present invention is the subsequent reversal of the binding at active sites on the arsenazo III substrate. Although the active sites of the substrate bind uranyl thereto when exposed to a sample containing uranyl, subsequent exposure of the substrate to 2,6-pyridinedicarboxylic acid reverses the uranyl binding and frees the uranyl from the arsenazo III. In this manner, the substrate can be used in subsequent applications.

Still another feature is the ability to chemically bind indicators, such as arsenazo III and bromocresol green, to flat surfaces, rather than to powder or beads, thereby allowing successful, permanent affixation of the indicator to substrates such as lens assemblies, quartz plates, microscope slides and the like that do not have to be made part of the sensing instrument. The advantage of this feature is that no sample need be prepared or collected nor are any reagents needed to make measurements. Also, because flat substrates such as glass slides and lens assemblies do not have to be incorporated as part of the sensing instrumentation, they can be changed out quickly, cleaned and/or restored, and reinstalled on the sensing instrumentation for subsequent applications.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a graphical representation of arsenazo III absorbance over a selected frequency range for samples with and without uranyl generated during testing of a preferred embodiment of the present invention; and FIG. 2 is a cross-sectional view of a fiber optic probe used in an embodiment of the present invention.

DETAILED DESCRIPTION OF A PREFERRED EMBODIMENT

The present invention, in its preferred embodiment, is a sensing device for detecting the presence and concentration of uranyl ($UO_2^{++}$) using the uranyl binding characteristics of arsenazo III and a substrate in an optical detection device.

Arsenazo III is a chemical substance that is sensitive to pH and the presence of uranyl. Arsenazo III has been found to react with uranyl and form a reaction product at its active site and undergo color changes in response to uranyl and pH, even when immobilized on a substrate. Thus, arsenazo III can be bound to any one of a number of substrate types, including flat surfaces, to be used as part of a sensing device for uranyl and pH.

When used for detecting the presence of uranyl, arsenazo III reacts irreversibly with uranyl to form a reaction product at its active site. This continues until the active site becomes saturated, at which point the sensor will cease binding uranyl thereto. Also, the rate at which uranyl binds to the active site of arsenazo III is related to the concentration of uranyl present in a fluid sample and also affects the overall absorbance of light passing through the substrate. Since the change in light absorbance is related to, if not proportional to the amount of uranyl bound at the site, the concentration of uranyl in the fluid sample can be determined through well-known absorbance analysis techniques using a spectrophotometer.

Preferably, arsenazo III is affixed permanently to any one of a number of different types of substrates by a chemical reaction sequence, which is discussed in more detail below. More preferably, arsenazo III is permanently bound to a substrate used in optical sensing devices, such as a glass plate or cellulose matrix. Most preferably, arsenazo III is bound to the lens assembly used in optical probes.

As is well known, optical sensing devices, such as optical probes, operate by positioning an indicator in a fluid sample of interest and measuring the difference in intensity between the light incident on the sample and light transmitted through or reflected from the fluid sample; the difference being representative of interaction between the indicator and a specific chemical constituent or groups of constituents present in the fluid sample. Depending on the indicator, such differences include fluorescence, color changes, and absorption. By absorption it is meant the decrease in intensity of light passing through the fluid sample as the result of the interaction of the incident light and the sample. By definition, absorption, also called optical density, is the logarithm (base 10) of the reciprocal of the transmittance, which is the ratio of the radiant power of the beam of light after it has passed through the fluid sample to the power of the incident beam.

Referring again to the present invention, once arsenazo III is permanently affixed to the optical sensing device, the optical sensing device is positioned in the fluid sample of interest. As discussed previously, uranyl present in the fluid sample reacts with the arsenazo III and begins forming a reaction product that binds to the optical sensing device at a rate related to the concentration of uranyl in the fluid sample. The binding of uranyl at the active site of the arsenazo III on the optical sensing device alters the absorbance characteristics of the fluid sample proportionately, thus allowing the concentration of uranyl to be determined using known optical analysis techniques.

For instance, arsenazo III or other indicators can be bound permanently to a cellulose matrix known for use in optical sensing devices. The cellulose matrix, which can be made of cotton cloth or similar material, is soaked in a solution containing arsenazo III for a preselected length of time to permanently bind arsenazo III thereto. In use, the matrix is mounted to the optical sensing device, which is used in its normal manner to measure the presence and concentration of uranyl in a fluid sample of interest.

For permanently binding arsenazo III to glass plates, lens assemblies and other similar substrates used in optical probes and other optical sensing devices, a more detailed method is necessary. Preferably, the binding method is a reactive sequence comprised of a Cleaning Step, a Silyation Step, an Amidization Step, a Reduction Step, a Diazotization Step and a Binding Step.

The Cleaning Step involves rinsing the substrate with acetone or similar compound and then rinsing the substrate with deionized water. Next, the substrate is heated for approximately 10 minutes in a 1% aqueous solution of sodium hydroxide at a temperature of approximately 90° C. The substrate is then removed and rinsed, once again, with deionized water. Then, the substrate is heated for approximately 2 minutes in a 5% aqueous solution of nitric acid at a temperature of approximately 50° C. Finally, the substrate is removed from the nitric acid solution and rinsed with deionized water.

The Silyation Step preferably includes placing the substrate in a 1% solution of 3-aminopropyltriethoxysilane (APTSI) in deionized water for approximately 15 minutes at room temperature. Once the substrate is removed and rinsed in deionized water, the substrate is cured at a temperature of approximately 110° C. for approximately 30 minutes. Silane coupling agents are necessary for activating the surface of the glass to provide a bond between the indicator and the glass. Many known silane coupling agents are known for use in silyation procedures and are understood to be satisfactory for this specific application.

The Amidization Step, which modifies the free end of the silane compound for further reaction, includes heating 29 mL chloroform and 1.5 mL triethylamine to a temperature of approximately 50° C., then adding approximately 0.52 grams of 4-nitrobenzoyl chloride. The substrate is placed in the resulting solution for approximately 15 minutes at a temperature of approximately 50° C. Next, the substrate is removed and rinsed with acetone, and then with deionized water. Finally, the substrate is allowed to dry.

The Reduction Step includes dissolving approximately 3.0 grams of sodium dithionite (sodium hydrosulfite, $Na_2S_2O_4 \cdot 2H_2O$) in 100 mL of deionized water (approximately 3–5% solution). The substrate is placed in the solution and heated at a temperature of approximately 35°–40° C. for approximately 45 minutes. Then, the substrate is removed from the solution and rinsed with deionized water.

The Diazotization Step includes dissolving approximately 0.25 grams of sodium nitrite ($NaNO_2$) in approximately 25 mL of 2M HCl. The solution is cooled in an ice-water bath or equivalent means and then the substrate is placed in the solution for approximately 30 minutes at a temperature of approximately 5° C. Finally, the substrate is removed from the solution and rinsed with cold deionized water.

The final step, the Binding Step, involves placing the substrate in a dilute acidic solution (having a pH of approximately 1–5) of the arsenazo III for approximately 30 minutes. Because indicators such as arsenazo III are not very soluble in water, only a small amount of the arsenazo III will dissolve. However, the resulting solution will be colored intensely. Next, the substrate is removed from the solution and rinsed with deionized water.

In addition to binding arsenazo III, a uranyl and pH indicator, the method just described allows other indicators to be bound permanently to substrates such as lens assemblies, glass plates and the like. Such indicators include but are not limited to bromocresol green, which is a known pH indicator in the range of approximately 4.5 (yellow) and 5.5 (blue). To bind bromocresol green (whose chemical name is tetrabromo-m-cresol sulfonphthalein) to a substrate of interest, the above steps are repeated, however, a dilute solution of bromocresol green, rather than arsenazo III, is used in the Binding Step.

Although permanently bound to the substrate, arsenazo III retains its sensitivity to pH in addition to its ability to bind uranyl at its active site. Similarly, bromocresol green maintains its sensitivity to pH even when bound permanently to the substrate. Therefore, both arsenazo III and bromocresol green can be used to detect pH in a manner that is well known in the prior art.

In the present invention, because the binding of uranyl at the active arsenazo III site is irreversible during exposure to uranyl, that is, the active sites bind uranyl until they become saturated and then no longer bind uranyl, the substrate can perform as an integrating sensor in which continuous binding causes cumulative buildup of uranyl on the sensor. For example, testing was conducted for determining the absorbance change of arsenazo III immobilized on a cellulose substrate exposed to a dilute (approximately 2.4 ppm) uranyl solution. The absorbance changes were monitored at a wavelength range from approximately 470 to 1100 nanometers (nm). It was found that the absorption peak occurred at approximately 628 nm and grows over time as uranyl from the dilute uranyl solution binds to the active site on the immobilized arsenazo III molecules. After a time period of approximately 18.5 hours, the uranyl concentration of the fluid sample was increased to approximately 4.8 ppm, however, no further change in absorbance was detected, thus indicating that the sensor was saturated.

Although uranyl forms a reaction product with arsenazo III and is bound to the arsenazo III substrate irreversibly during exposure of uranyl, the exposure of the substrate to 2,6- pyridinedicarboxylic acid reverses the binding whereby the uranyl is freed from the substrate. Thus, the substrate can be restored for subsequent use. In the testing described above, the subsequent addition of a 200-fold molar excess of 2,6-pyridinedicarboxylic acid to the uranyl solution effectively restored the cellulose substrate to its pre-testing condition by reversing the uranyl response.

FIG. 1 shows the spectra of arsenazo III bound to a glass microscope slide before and after exposure to a 50 parts per million (ppm) uranyl solution. Using an ultraviolet-visible diode array spectrophotometer, the absorbance was measured at a wavelength range from approximately 350 to 800 nm.

A first absorption spectrum 12 was measured prior to exposing the microscope slide to a fluid sample having uranyl. Next, the microscope slide was exposed to a fluid sample comprised of a 50 ppm uranyl solution and a second absorption spectrum 14 was measured. As can be seen in FIG. 1, the absorbance of second absorption spectrum 14 is greater than the absorbance of first absorption spectrum 12 from approximately 350 nm until a wavelength of approximately 490 nm, then remains less than first absorption spectrum 12 up until approximately 590 nm. Thereafter, second absorption spectrum 14 remains greater than first absorption spectrum 12 throughout the test range, with the largest disparity in absorbance occurring between approximately 630 to 680 nm.

Thus, at selected wavelengths, the measured absorbance of an arsenazo III substrate is greater in the presence of uranyl, particularly at the upper end of the tested wavelength range. As previously discussed, the increased absorbance is attributable to uranyl present in the fluid sample binding to the active site of the arsenazo III-bound substrate.

The convenience with which substrates having permanently-affixed indicators, such as arsenazo III and bromocresol green, can be installed to optical sensing devices expands the possible applications for such sensing devices, especially remote applications by optical sensing devices. Thus, substrates having permanently-affixed indicators can be used with optical probes, for instance with a probe 20, as shown in FIG. 2. Probe 20 represents just one of several applications in which the present invention is applicable. Virtually all sensing instrumentation that employs lens assemblies, glass slides, quartz lens and similar substrates can make use of the permanent binding method of the present invention.

Probe 20, one of several possible instruments for which the present invention is suited, preferably comprises a threaded fiber holder 22 holding an optical transmission fiber 24 and an optical collection fiber 26, a housing 28 for receiving threaded fiber holder 22, a substrate 32 having an indicator permanently affixed thereto, and a screen 34 permeable to a fluid sample 36 of interest.

Substrate 32 is preferably positioned within housing 28 so that a first side 42 of substrate 32 is spaced apart from the distal ends 31, 33 of optical transmission and collection fibers 24, 26, respectively. Screen 34 is preferably integral with a distal end 44 of housing 28 so that screen 34 is spaced apart from a second side 46 of substrate 32 and allows a portion of fluid sample 36 to pass therebetween to contact second side 46 of substrate 32.

In previous probes, in which the indicator was not permanently incorporated into substrate 32, screen 34 needed to be positioned adjacent to second side 46 of substrate 32 to hold an indicator membrane against substrate 32 while simultaneously allowing a portion of fluid sample 36 to come in contact with the indicator membrane. However, in probe 20, because the indicator is permanently affixed to second side 46 of substrate 32, such requirement has been eliminated.

Substrate 32 is preferably a glass or quartz lens assembly, glass plate or other suitable material receptive to light transmission and having arsenazo III or other appropriate indicators permanently affixed thereto using the reactive sequence discussed above. Housing 28 is preferably a nut, such as a Swagelok nut, having a threaded inner surface 48 forming an opening dimensioned to threadably receive threaded fiber holder 22 therein. Obviously, depending on the application, threaded fiber holder 22 and housing 28 can be extended to protect more of transmission and collection fibers 24, 26.

In use, distal end 44 of probe 20 is inserted into the location of fluid sample 36. Preferably, probe 20 is optically coupled to an ultraviolet-visible diode array spectrophotometer (not shown) or similar equipment for measuring absorbance, a computer for data acquisition and means for data analysis. Alternatively, probe 20 can be operably placed near a photodetector (not shown), which measures the light intensity and generates an electrical signal proportional thereto.

As discussed previously, a portion of fluid sample 36 passes through screen 34 and comes in contact with second side 46 of substrate 32. As fluid sample 36 comes in contact with second side 46 of substrate 32, uranyl present in fluid sample 36 binds irreversibly to second side 46 of substrate 32 at a rate related to the concentration of uranyl in fluid sample 36. Light transmitted from transmission fiber 24 passes through the portion of fluid sample 36 occupying the spacing between second side 46 of substrate 32 and screen 34, is reflected off of screen 34, received in substantial part by collection fiber 26, which is in optical communication with the absorbance measuring equipment, as discussed above.

Using the necessary absorbance measuring equipment, absorbance measurements of light passing through substrate 32 are taken over a broad range of wavelength frequencies, similar to experimental testing, described above. From the collected data, the concentration of uranyl in fluid sample 36 can be determined. Once the application has been completed, probe 20 is removed from fluid sample 36 and substrate 32 is exposed to 2,6-pyridinedicarboxylic acid to reverse the binding and free the uranyl from second side 46 of substrate 32. Probe 20 is then ready to be used again. Alternatively, screen 34 can be removed so that substrate 32 can be removed quickly and replaced with a new or restored substrate. Substrate 32, which was just removed, can then be restored and reused in another probe or in probe 20 in a later application.

Alternatively, substrate 32 and sensor probe 20 could be used with samples that scatter or reflect light or that have light scattering particles that cause a portion of the light transmitted into the sample to be scattered and, to a certain extent, scattered back toward the collection fiber, thereby being made available for collection. Also, substrate 32 can be used in other types of optical sensing probes, such as the commonly assigned and co-pending spectrophotometric probe serial number 07/953,042.

Finally, in addition to determining the presence and measuring the concentration of uranyl in fluid sample 36, arsenazo III can be used to measure the pH of fluid sample 36. Similarly, as discussed previously, bromocresol green can be used to determine the pH of fluid sample 36.

It will be apparent to those skilled in the art that many changes and substitutions can be made to the preferred embodiment herein described without departing from the spirit and scope of the present invention as defined by the appended claims.

What is claimed is:

1. Apparatus for indicating the presence of a concentration of a substance in a sample, said apparatus for use with means for transmitting and receiving light, said apparatus comprising:

an indicator that reacts with said substance to form a reaction product with said substance; and a substrate translucent to said light, said indicator being chemically immobilized on said substrate so that, when said sample contacts said substrate and said indicator forms said reaction product on said substrate and said light is transmitted through said substrate by said transmitting and receiving means, said reaction product absorbs a portion of said light, said reaction product absorbing said portion of said light in proportion to said concentration of said substance; and means in optical communication with said substrate for determining said concentration from said light received from said substrate.

2. The apparatus as recited in claim 1, wherein said indicator is immobilized on said substrate by soaking said substrate in a solution containing said indicator for a preselected length of time.

3. The apparatus as recited in claim 1, wherein said substance is uranyl and wherein said indicator is arsenazo III.

4. The apparatus as recited in claim 1, wherein said reaction product indicates a pH for said sample and wherein said indicator is bromocresol green.

5. The apparatus as recited in claim 1, wherein said indicator is immobilized to said substrate by a method comprising the steps of:

silyating said substrate by
soaking said substrate in a silane coupling solution, and then curing said substrate;

amidizing said substrate by
soaking said substrate in a solution containing chloroform, triethylamine and 4-nitrobenzoyl chloride;

reducing said substrate by
soaking said substrate in a reducing solution, and then heating said substrate;

diazotizating said substrate by
soaking said substrate in a solution containing sodium nitrite and hydrochloric acid,
cooling said substrate, and then
rinsing said substrate with a cleaning solution; and
placing said substrate in a solution containing said indicator for a preselected length of time.

6. The apparatus as recited in claim 1, wherein said substrate is selected from the group consisting of glass lenses, glass microscope slides, glass wool, quartz lenses, quartz rods, quartz plates and cellulose matrices.

7. The apparatus as recited in claim 1, wherein said light transmitting and receiving means further comprises optical fibers, and wherein said apparatus further comprises a housing having a proximal end and a distal end, said substrate attached to said distal end.

8. A method for determining a concentration of uranyl in a sample, said method comprising the steps of:

placing a substrate having a uranyl-responsive indicator chemically immobilized thereon in said sample so that said indicator comes in contact with said sample, said indicator binding said uranyl to form a reaction product;

transmitting light through said substrate, said indicator absorbing a portion of said light in proportion to said concentration of said uranyl;

collecting light transmitted through said substrate; and comparing said transmitted light to said collected light to determine the absorbance of said reaction product in said sample whereby said concentration can be determined.

9. The method as recited in claim 8, further comprising the step of exposing said substrate to 2,6-pyridinedicarboxylic acid whereby said uranyl is freed from said indicator.

10. The method as recited in claim 8, wherein said indicator is arsenazo III.

11. The method as recited in claim 8, wherein said substrate is a cellulose matrix and wherein said indicator is immobilized thereon by dyeing said cellulose matrix with a solution containing said indicator.

12. The method as recited in claim 8, wherein said substrate is selected from the group consisting of fiber optic lens assemblies, glass lenses, glass microscope slides, glass wool, quartz lenses, quartz rods and quartz plates.

13. The method as recited in claim 8, wherein said method is for use with a first optical fiber and a second optical fiber, and said transmitted light is transmitted by said first optical fiber and said collected light is collected by said second optical fiber, and said method further comprises the step of reflecting said light passing through said substrate to said second optical fiber.

14. The method as recited in claim 8, wherein said indicator is immobilized thereon by a method comprising the steps of:

rinsing said substrate with at least one cleaning solution;

silyating said substrate by
soaking said substrate in a silane solution for a first preselected length of time, and then
curing said substrate for a second preselected length of time;

amidizing said substrate by
soaking said substrate in a solution containing chloroform, triethylamine and 4-nitrobenzoyl chloride for a third preselected length of time,
cooling said substrate for a fourth preselected length of time, and then
rinsing said substrate with a cleaning solution;

reducing said substrate by
soaking said substrate in a reducing solution for a fifth preselected length of time;

diazotizating said substrate by
soaking said substrate in a solution containing sodium nitrite and hydrochloric acid for a sixth preselected length of time, and then
rinsing said substrate with a cleaning solution; and soaking said substrate in a solution containing said indicator for a seventh preselected length of time.

15. A method for immobilizing an indicator to a substrate, said substrate for use in detecting the presence of a substance in a fluid sample, said method comprising the steps of:

rinsing said substrate with at least one cleaning solution;

silyating said substrate by
soaking said substrate in a silane solution for approximately 15 minutes, and then
curing said substrate for approximately 30 minutes at a temperature of approximately 110° C.;

amidizing said substrate by
soaking said substrate in a solution containing chloroform, triethylamine and 4-nitrobenzoyl chloride for approximately 15 minutes at a temperature of approximately 50° C.;

reducing said substrate by
soaking said substrate in a reducing solution heated at a temperature within a range of approximately 35°–40° C. for approximately 45 minutes;

diazotizating said substrate by
soaking said substrate in a solution containing sodium nitrite and hydrochloric acid for approximately 30 minutes at a temperature of approximately 5° C., and then
rinsing said substrate with a cleaning solution; and binding said indicator to said substrate by
soaking said substrate in a solution containing said indicator for approximately 30 minutes,
removing said substrate from said solution, and then
rinsing said substrate with a cleaning solution.

16. The method as recited in claim 15, wherein said indicator is arsenazo III for detecting uranyl in said sample.

17. The method as recited in claim 15, wherein said indicator is bromocresol green for indicating pH in said sample.

18. The method as recited in claim 15, wherein said substrate is selected from the group consisting of glass lenses, glass microscope slides, glass wool, quartz lenses, quartz rods and quartz plates.

19. The method as recited in claim 15, wherein said substrate is a cellulose matrix and wherein said binding step further comprises dyeing said cellulose matrix with said indicator.

* * * * *